US00PP20745P3

(12) United States Plant Patent
Clark et al.

(10) Patent No.: US PP20,745 P3
(45) Date of Patent: Feb. 9, 2010

(54) GRAPE PLANT NAMED 'A-2640'

(50) Latin Name: ***Vitis* hybrid (*Vitis labrusca* L.×*Vitis vinifera* L.)**
Varietal Denomination: A-2640

(75) Inventors: John Reuben Clark, Fayetteville, AR (US); James Norman Moore, Fayetteville, AR (US)

(73) Assignee: The Board of Trustees of the University of Arkansas, N.A., Little Rock, AR (US)

( * ) Notice: Subject to any disclaimer, the term of this patent is extended or adjusted under 35 U.S.C. 154(b) by 0 days.

(21) Appl. No.: 12/157,392

(22) Filed: Jun. 10, 2008

(65) Prior Publication Data

US 2009/0307810 P1 Dec. 10, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H. Para
*Assistant Examiner*—Louanne C Krawczewicz Myers
(74) *Attorney, Agent, or Firm*—Jondle & Associates, P.C.

(57) ABSTRACT

A grape cultivar particularly distinguished by large, seedless, black-skinned berries, large clusters, with a mid to late season of ripening, high productivity and good vine health, is disclosed.

1 Drawing Sheet

GENUS AND SPECIES

*Vitis* hybrid (*Vitis labrusca* L.×*Vitis vinifera* L.)

Variety Denomination

'A-2640'

BACKGROUND OF THE NEW PLANT

The present invention comprises a new and distinct cultivar of *Vitis,* botanically known as *Vitis* hybrid (*Vitis labrusca* L.×*Vitis vinifera* L.), and hereinafter referred to by the cultivar name 'A-2640'. 'A-2640' originated from a hand-pollinated cross of the female *Vitis labrusca* L.×*Vitis vinifera* L. 'Arkansas Selection 1925' (unpatented) with the male *Vitis labrusca* L.×*Vitis vinifera* L. 'Arkansas Selection 2020' (unpatented) made in 1992 near Clarksville, Ark. (west-central Ark.).

The seeds resulting from the controlled hybridization were germinated in a greenhouse during the winter of 1992-1993 and the resulting seedlings were planted in the spring of 1993 in a vineyard at Clarksville, Ark. The seedlings fruited in the summer of 1996 and a single selection designated 'Arkansas Selection 2640' was selected for its large seedless, oblong fruits with no seed traces, neutral flavor, large clusters, and overall very good fruit quality.

During 1996, 'Arkansas Selection 2640' was propagated asexually in Clarksville, Ark. by rooting hardwood cuttings. A test planting of three vines of 'Arkansas selection 2640' was established and the instant plant was subsequently given the final variety name 'A-2640'. Subsequently, larger test plantings were established with asexually multiplied vines in Clarksville, Ark. and near Delano, Calif. (Kern County). In all propagations, hardwood cuttings were used. 'A-2640' roots readily from hardwood cuttings. All propagules (resulting plants) of 'A-2640' have been observed to be true to type through successive asexual propagations and the vegetative and fruit characteristics of the original plant have been maintained. All vines planted from hardwood cutting propagation fruited in the second or third season of growth in the vineyard after planting.

Test plantings at the above two locations have shown 'A-2640' to be most adapted to the Delano, Calif. test site, where the vines produce consistently high yields of fruit with large berries and clusters along with no fruit cracking at maturity. In Arkansas, 'A-2640' has excellent fruit quality and no seed traces, but a substantial limitation observed is fruit cracking following rainfall when fruits are ripe.

The new cultivar was discovered in Clarksville, Ark. and has been asexually reproduced repeatedly by rooting hardwood cuttings over a 12-year period. The present invention has been found to retain its distinctive characteristics through successive asexual propagations.

SUMMARY OF THE INVENTION

The following are the most outstanding and distinguishing characteristics of the new cultivar when grown under normal horticultural practices in west-central Ark. and Delano, Calif.

1. Vines having medium to high vigor, with an upright growth habit characteristic of *Vitis vinifera;*
2. Produces well-rooted plants;
3. The fruit ripens in the mid-to-late season, with the average first harvest date being August 20 in west-central Ark. and Delano, Calif.;
4. The fruit quality is maintained well on the vine after maturity and the fruit quality for marketing is maintained for up to two to three weeks on the vines after initial maturity is reached;
5. Berries that adhere well to the fruit pedicel and do not shatter from the clusters during growth or harvest;
6. Black-skinned berries at early maturity. The fruit is evenly colored within the cluster and the berries are oblong-shaped;
7. Fruit skins that are medium-thick and adhere to the flesh;

8. Berries that are medium-large in size (about 4.5 g) and a flesh flavor that is neutral and sweet with soluble solids concentration of the juice at fruit maturity averaging 18% with low to medium acidity;
9. Fruit that is of the stenospermocarpic type of seedlessness and contains small, soft vestigial seed traces that are not noticeable when eaten; and
10. Fruit clusters that are borne usually two per shoot, are large, well-filled, but not overly tight. Fruit cluster peduncles are medium-long and easy to remove from the supporting shoots during harvest.

DESCRIPTION OF THE PHOTOGRAPHS

This new *Vitis* hybrid plant is illustrated by the accompanying photographs which show a representative bunch of grapes, foliage and segments of vines; the colors shown are as true as can be reasonably obtained by conventional photographic procedures.

DESCRIPTION OF THE NEW CULTIVAR

Figure 1:
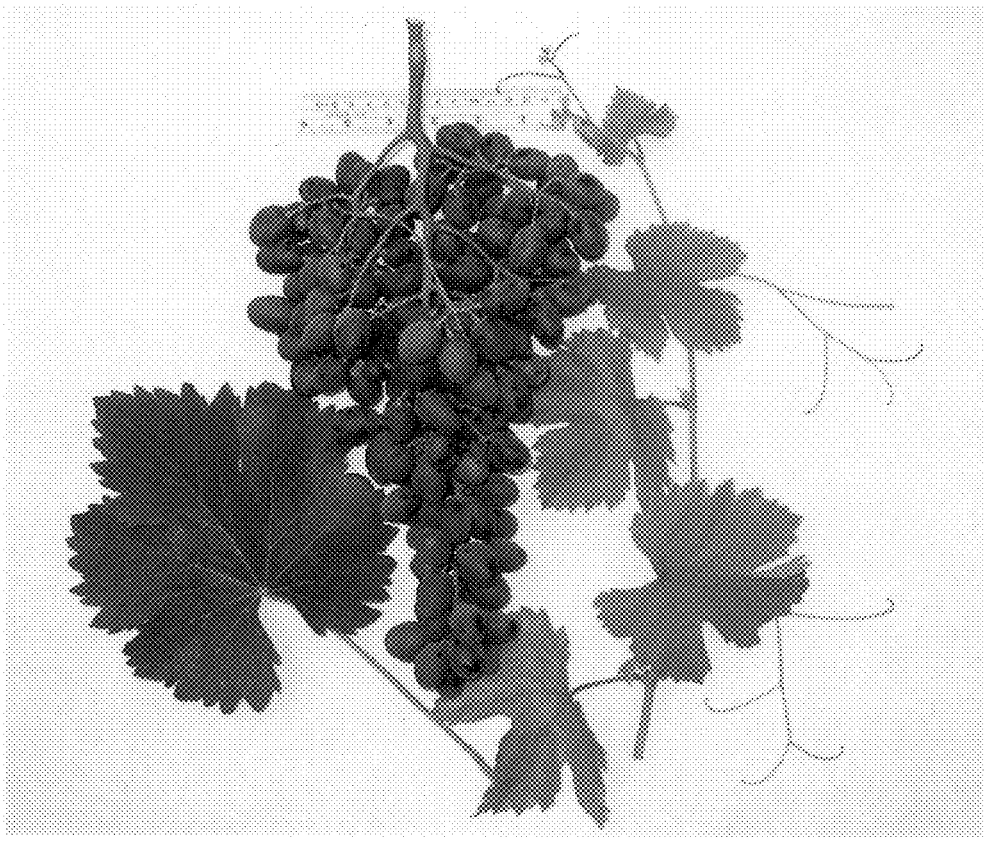
FIG. 1 shows a representative bunch of grapes, foliage and segments of vines.
Figure 2:
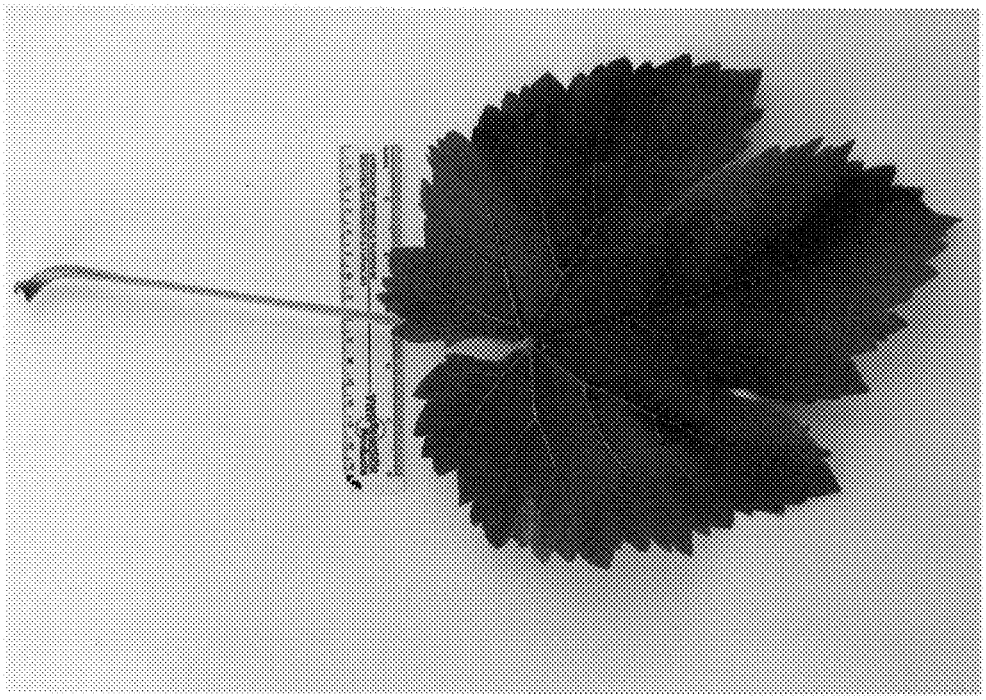
FIG. 2 shows a close-up of a mature leaf.

The following detailed descriptions set forth the distinctive characteristics of 'A-2640'. Where dimensions, sizes, and other characteristics are given, it is to be understood that such characteristics are approximations of averages set forth as accurately as practicable. The colors are as nearly true as is reasonably possible in a color representation of this type. The plant history and descriptions are taken from specimens grown at Delano, Calif. unless otherwise indicated. Vines used for measurement were irrigated using trickle (drip) irrigation. The majority of the data collection was from vines that were 5-years-old unless otherwise indicated. The color readings were determined under natural light. Color references are to the RHS Colour Chart of The Royal Horticultural Society of London (RHS) (2001).

DESCRIPTION OF THE NEW PLANT

Classification:

*Family.*—Vitaceae.

*Botanical name.*—*Vitis* hybrid (*Vitis labrusca* L.×*Vitis vinifera* L.).

*Common name.*—Grapevine.

*Denomination.*—'A-2640'.

Parentage:

*Female parent.*—The *Vitis labrusca* L.×*Vitis vinifera* L. 'Arkansas Selection 1925' (unpatented).

*Male parent.*—The *Vitis labrusca* L.×*Vitis vinifera* L. 'Arkansas Selection 2020' (unpatented).

Vine:

*Size.*—Medium.

*Growth.*—Moderately vigorous to vigorous.

*Density of foliage.*—Medium.

*Productivity.*—Very productive.

*Rootstock.*—Vines are grown and tested on their own-rooted vines.

*Cold hardiness.*—Hardy to −15° C.

*Trunk.*—Shape: Slender. Straps: Long, split. Surface texture: Shaggy. Inner bark color: RHS 177B (Greyed-Orange). Diameter: 20.67 cm for eight year old vines at a height of 1.0 m above the ground.

*Shoots* (*current-season canes*).—Shoot tips: Slightly open; RHS 145A (Yellow-Green) shoot tips have very weak RHS 61A (Red-Purple) anthocyanin present in the shoots and the distribution of anthocyanin is absent at the tip. Density of prostrate hairs: Very dense. Density of erect hairs: Absent. Shape: Rounded. Length: 157.6 cm at 2.5 months after budbreak. Diameter: 1.2 cm at 2.5 months after budbreak in the middle of the first two nodes from the attachment point. Vigor during flowering: Very strong. Attitude during flowering on shoots which are not tied: Horizontal. Color of dorsal and ventral sides of internodes: RHS 144A (Yellow-Green). Color of dorsal and ventral sides of nodes: RHS 144A (Yellow-Green). Density of erect hairs on nodes and internodes: Absent. Density of prostrate hairs on nodes: Very sparse. Anthocyanin coloration of buds: Absent.

*Tendrils.*—General: Trifurcated with medium thickness and a discontinuous distribution at full flowering. Length (measured at full flowering): Very long, 30 cm. Color (at full flowering): RHS 145A (Yellow-Green). Number of consecutive tendrils: Up to two. Pattern: Flowering node $4^{th}$ to $5^{th}$, then followed by tendrils on $6^{th}$, $8^{th}$, $9^{th}$, $11^{th}$, $12^{th}$, $14^{th}$, $15^{th}$ nodes.

Buds:

*General.*—Basal buds are most fruitful and seldom dead.

*Time of budbreak.*—Medium; about March 3.

*Shape.*—Pointed.

Canes (mature canes):

*Length.*—249.8 cm.

*Shape.*—Stocky.

*Surface texture.*—Striate.

*Internode length.*—Long, 14.0 cm.

*Width at node.*—1.28 cm.

*Cross section.*—Circular.

*Color.*—RHS 166D (Greyed-Orange).

*Density of erect hairs of nodes and internodes.*—None or very sparse.

*Growth of axillary shoots from the mature cane.*—57.4 cm.

*Lenticels.*—Quantity: 47 per 0.5 $cm^2$. Shape: Round but occasionally oblong. Length: 0.12 cm. Width: 0.03 cm. Color: RHS 202 A (Black).

Leaves:

*Immature* (*unfolded,* $4^{th}$ *distal*).—Color: RHS 146A (Yellow-Green). Pubescence density: Prostrate hairs between veins: Very dense. Erect hairs between veins: Very sparse. Prostrate hairs on veins: Dense. Erect hairs on veins: Medium. Anthocyanin coloration of six distal leaves prior to flowering: Weak, RHS 61A (Red-purple) but appears coppery from being diffused with the yellow-green background color of the leaves.

*Mature.*—Type: Simple, alternate. Shape: Pentagonal. Profile: Involute. Apex: Occurs in the plane of the leaf; obtuse. Base: Cordate. Margin: Serrated. Quantity of lobes: 3 to 5. Serration: Entire. Tooth length: 0.93 cm on the middle tooth of the basal lobe. Tooth width: 1.54 cm on the middle tooth of the basal lobe. Tooth shape: Incised. Quantity of teeth per lobe: About 10.2. Number of teeth per leaf: About 51. Size: Very large; height is 11.3 cm, length is 18.0 cm and width is 23.6 cm. Thickness: Medium. Shape of petiole sinus: Slightly open. Tooth at petiole sinus:

Absent. Petiole sinus limited by veins: Absent. Shape of upper lateral sinus: Open. Depth of upper lateral sinus: Shallow. Margin undulation: Pronounced undulation with overall undulation between the main and lateral veins; small ratio length/width. Upper surface: Color: RHS 146A (Yellow-Green). Surface texture: Rugose, dull in appearance; pubescence present on veins. Lower surface: Color: RHS 146B (Yellow-Green). Surface texture: Rugose, dull in appearance, glossiness is weak. Anthocyanin vein coloration: Absent. Pubescence density: Prostrate hairs between veins: Medium. Erect hairs between veins: Very sparse. Prostrate hairs on main veins: Medium. Erect hairs on veins: Medium.

*Petiole.*—Length: Very long (23.9 cm), much longer when compared to middle vein. Diameter: 0.33 cm. Pubescence: Density of prostrate hairs: Sparse. Density of erect hairs: Sparse; sinus. Shape of base of petiole sinus: V-shaped. Color: RHS 144B (Yellow-Green).

Flowers:

*Sex/Type.*—Hermaphrodite, borne in a cluster of flowers (inflorescence).

*Quantity of flowers per cluster.*—486.2.

*Quantity of flower clusters per vine (plant).*—About 35.2.

*Quantity of individual flowers per vine (plant).*—About 17, 114.24.

*Fragrance.*—Absent.

*Flower depth.*—0.3 cm.

*Flower width.*—0.19 cm.

*Inflorescence length.*—Very long, 32.1 cm.

*Quantity of inflorescences.*—2 to 3 per shoot.

*Date of Bloom.*—Mid-season; first bloom is about May 7 and full bloom is about mid-May.

*Petals.*—Quantity per flower and appearance: 5, petals are fused into a cap, or calyptra, which dehisce from the base at the time of bloom. Length: 0.23 cm. Width: 0.11 cm. Apex: Acute. Base: Truncate. Margin: Entire. Color, upper surface: RHS 144A (Yellow-green). Color, lower surface: RHS 144A (Yellow-green).

*Sepals.*—Absent.

Reproductive organs:

*Stamens.*—Aspect: Erect. Quantity per flower: 5 or 6. Anther: Length: 0.13 cm. Width: 0.1 cm. Color: RHS 143A (Green). Pollen: Quantity: Abundant. Color: RHS 13C (Yellow).

*Pistil.*—Size, general: Medium-long. Quantity per flower: 1. Stigma: Quantity: 1. Length: 0.036 cm. Width: 0.072 cm. Color: RHS 154D (Yellow-green). Style: Quantity: 1. Length: 0.038 cm. Width: 0.060 cm. Color: RHS 143A (Green). Ovary: Quantity: 1. Length: 0.096 cm. Diameter: 0.124 cm. Color: RHS 143A (Green).

Fruit:

*Maturity.*—Medium-late; 20 days after 'Thompson' (unpatented); first harvest date is approximately August 20 .

*Berry.*—Seed presences: Seedless, rudimentary seed traces are present but very small. Size/Weight: Medium-large, 4.5 g per berry and uniform in size. Shape: Oblong; cross section circular; length 2.40 cm; width 1.74 cm. Color (skin): RHS 202A (Black). Flesh: Non-slipskin, crisp; medium-firm; juicy; very slight anthocyanin color in flesh where flesh contacts the skin (to the depth of the skin); the flesh has a very slight RHS 83A (Violet) that extends to about 1/10 of a millimeter into the flesh while the rest of the flesh does not have a distinct color but is overall translucent. Brush length: Medium. Soluble solids: 18%. Acidity: Low to medium; 0.46 g/100 mL expressed as tartaric acid. Flavor: Neutral and sweet. Skin: Thickness is medium; texture is medium; reticulation absent; roughness absent; tenacious to flesh; bloom is medium; ground and blush colors are absent. Pedicel length: Intermediate; berry separation from pedicel medium; the diameter is 0.042 cm and the length is 0.142 cm. Hilum visibility: Unclear. Eating quality: Very good with good crispness and a mostly neutral flavor and sweet. Shipping quality: Good, with good berry retention to the pedicel. Tendency to crack: There is little tendency to crack unless rainfall occurs at full-maturity which can lead to some cracking or splitting of the skin.

*Cluster.*—Mature cluster weight: Very large; 1,135 g. Mature cluster length: Very long; 38.0 cm. Mature cluster width: Medium; 21 cm. Quantity of berries per cluster: 277. Density: Medium loose. Form: Conical. Peduncle: Length: Very long; 7.1 cm. Lignification: Medium. Color: RHS 144A (Yellow-Green).

Disease and insect resistance: The new cultivar is moderately resistant to powdery mildew (*Uncinula necator* Burr.) but is susceptible to downy mildew (*Plasmopora viticola* Berl. & Tomi.), black rot (*Guignardia bidwellii* (Ell.) V. & R.), and anthracnose (*Elsinoe ampelina* (d. By.) Sher). Fungal diseases can be controlled by the use of available fungicides.

Use: For fresh-market use

COMPARISON WITH PARENTAL AND COMMERCIAL CULTIVARS

'A-2640' differs from the female parent, the female *Vitis labrusca* L.×*Vitis vinifera* L. 'Arkansas Selection 1925' (unpatented) in that 'A-2640' is a seedless grape, while 'Arkansas Selection 1925' is a seeded grape. Additionally, 'Arkansas Selection 1925' ripens approximately one week before 'A-2640'.

'A-2640' differs from the male parent, the *Vitis labrusca* L.×*Vitis vinifera* L. 'Arkansas Selection 2020' (unpatented) in that 'A-2640' has oblong-shaped berries, while 'Arkansas Selection 2020' has semi-oval-shaped fruit. Additionally, 'Arkansas Selection 2020' has a lighter flesh color than 'A-2640'.

'A-2640' differs from the commercial cultivar 'Jupiter' (U.S. Plant Pat. No. 13,309) in that 'A-2640' is less hardy in cold winters than 'Jupiter'.

What is claimed is:

1. A new and distinct cultivar of grape plant as shown and described herein.

* * * * *